(12) United States Patent
Ouyang et al.

(10) Patent No.: US 7,195,134 B2
(45) Date of Patent: Mar. 27, 2007

(54) DOSAGE COUNTING DEVICES

(75) Inventors: Tianhong Ouyang, Chapel Hill, NC (US); Geoff Brace, Raleigh, NC (US)

(73) Assignee: Bespak plc, Norfolk (GB)

( * ) Notice: Subject to any disclaimer, the term of this patent is extended or adjusted under 35 U.S.C. 154(b) by 443 days.

(21) Appl. No.: 10/468,804

(22) PCT Filed: Feb. 22, 2002

(86) PCT No.: PCT/GB02/00813

§ 371 (c)(1),
(2), (4) Date: Mar. 9, 2004

(87) PCT Pub. No.: WO02/069253

PCT Pub. Date: Sep. 6, 2002

(65) Prior Publication Data

US 2004/0149772 A1 Aug. 5, 2004

(30) Foreign Application Priority Data

Feb. 23, 2001 (GB) ................................. 0104558.2

(51) Int. Cl.
*B67D 5/22* (2006.01)
(52) U.S. Cl. .................................. 222/36; 128/205.23
(58) Field of Classification Search .................. 222/23, 222/30, 32, 36, 38, 22; 128/200.23, 205.23, 128/200.14, 200.18, 200.24; 116/308, 309
See application file for complete search history.

(56) References Cited

U.S. PATENT DOCUMENTS

| | | | |
|---|---|---|---|
| 5,228,586 A | 7/1993 | Fuchs | |
| 5,382,243 A * | 1/1995 | Mulholland | 604/301 |
| 5,421,482 A | 6/1995 | Garby et al. | |
| 5,482,030 A * | 1/1996 | Klein | 128/200.23 |
| 5,611,444 A | 3/1997 | Garby et al. | |
| 5,687,710 A | 11/1997 | Ambrosio et al. | |
| 5,718,355 A | 2/1998 | Garby et al. | |
| 5,740,972 A | 4/1998 | Matthew | |
| 5,799,651 A | 9/1998 | Garby et al. | |
| 5,829,434 A | 11/1998 | Ambrosio et al. | |
| 5,988,496 A | 11/1999 | Bruna | |
| 6,161,724 A * | 12/2000 | Blacker et al. | 222/23 |
| 6,164,494 A | 12/2000 | Marelli | |
| 6,679,251 B1* | 1/2004 | Gallem et al. | 128/200.23 |
| 6,953,039 B2* | 10/2005 | Scarrott et al. | 128/200.14 |

FOREIGN PATENT DOCUMENTS

| | | |
|---|---|---|
| EP | 0 480 488 | 4/1992 |
| EP | 1 065 477 | 1/2001 |
| GB | 1 317 315 | 5/1973 |

(Continued)

*Primary Examiner*—Lien M. Ngo
(74) *Attorney, Agent, or Firm*—Smith, Gambrell & Russell LLP

(57) ABSTRACT

Apparatus comprising a housing (1) defining a (2) portion for receiving in use a dose-dispensing container (20), the housing containing a dose counter comprising at least one annular counter member (141, 142), a helix-like coil (143) and transmission means (144) for operatively connecting the helix-like coil and the at least one annular counter member, wherein movement of the received dose-dispensing container acts to compress the helix-like coil to thereby rotate the transmission means and the at least one annular counter member.

20 Claims, 2 Drawing Sheets

Figure 1:
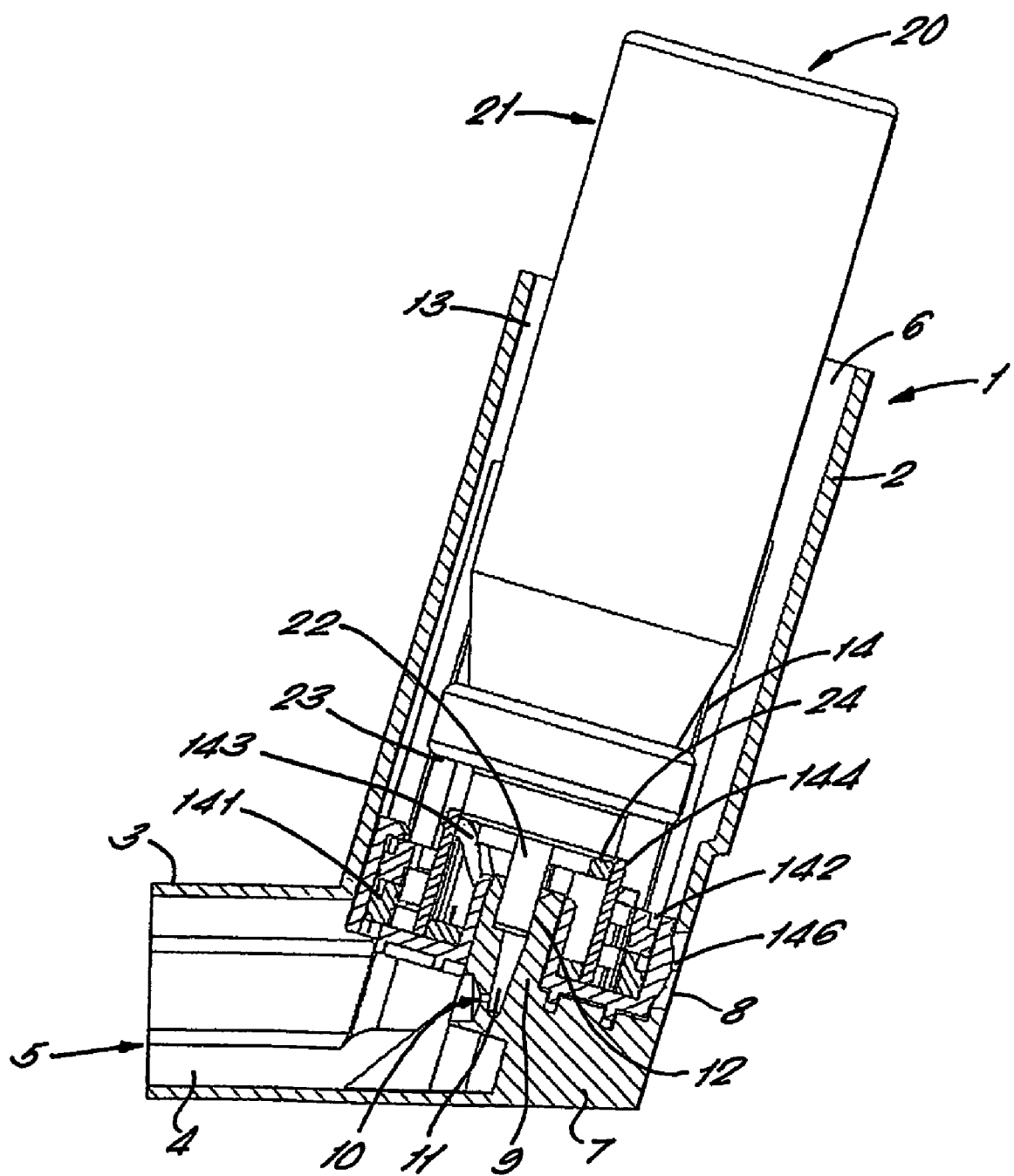

| | FOREIGN PATENT DOCUMENTS | | WO | WO 95/08484 | 3/1995 |
|---|---|---|---|---|---|
| | | | WO | WO 02/067844 | 9/2002 |
| GB | 2 372 541 | 8/2002 | WO | WO 02/069252 | 9/2002 |
| GB | 2 372 542 | 8/2002 | | | |
| GB | 2 372 543 | 8/2002 | * cited by examiner | | |

DOSAGE COUNTING DEVICES

The present invention relates to counting devices for use with dose-dispensing delivery apparatus which require an axial force for operation.

It has been recognised that there is a need to provide accurate information to the user of a dose-dispensing delivery apparatus concerning the number of doses delivered from, or remaining in, the apparatus. Without such accurate information there is the danger that a user will forget how many doses have been delivered and hence take a greater or fewer number of doses than is required. There is also the danger that a user may be unaware that the delivery apparatus is empty or close to empty. Hence, in an emergency situation, the user may seek to take a dose from the delivery apparatus only to find that there are no doses left in the apparatus. This is especially dangerous where the delivery apparatus is for use in dispensing medicinal compounds for the treatment of chronic or acute symptoms, for example, as in the case of a pressurised metered dose inhaler used for treating asthmatic reactions.

A number of devices have been proposed to count the number of doses delivered or remaining in a delivery apparatus. WO95/08484 teaches a dose counting device for use with an aerosol medication dispenser. The device works by translating a non-rotative force on an outer cover into a rotation of an indicator wheel by use of a set of flexible pawls engaged with a set of teeth. The pawls depress and thereby extend circumferentially when the applied force forces them to effect a rotation of the teeth. This device has, however, been found to have disadvantages. The reliability of operation of the counting device depends on the relationship between the stiffness of the internal spring bias of the medication dispenser and the pawls. If the pawls are too stiff relative to the internal spring bias then the medication dispenser may dispense a dose before the pawls flex sufficiently to rotate the indicator wheel; a dose wold be delivered without the counter registering it. Alternatively, if the pawls are too flexible relative to the internal spring bias then the pawls may flex sufficiently to rotate the indicator wheel before the medication dispenser has dispensed a dose; a dose would be registered by the counter but not actually delivered.

The present invention seeks to provide a dosage counting device which overcomes these problems.

Accordingly, the present invention provides apparatus comprising a housing defining a portion for receiving in use a dose-dispensing container, the housing containing a dose counter comprising at least one annular counter member, a helix-like coil and transmission means for operatively connecting the helix-like coil and the at least one annular counter member, wherein movement of the received dose-dispensing container acts to compress the helix-like coil to thereby rotate the transmission means and the at least one annular counter member.

The present invention also provides apparatus comprising a housing defining a portion for receiving in use a dose-dispensing container, the housing containing a dose counter comprising at least one annular counter member, a helix-like coil and transmission means for operatively connecting the helix-like coil and the at least one annular counter member, and a support for supporting the at least one annular counter member, helix-like coil and transmission means in proper alignment with the received dose-dispensing container, wherein the support is an interference fit in the housing such that a first actuation of the received dose-dispensing container sets the position of the support relative to the received dose-dispensing container and housing.

Figure 2:
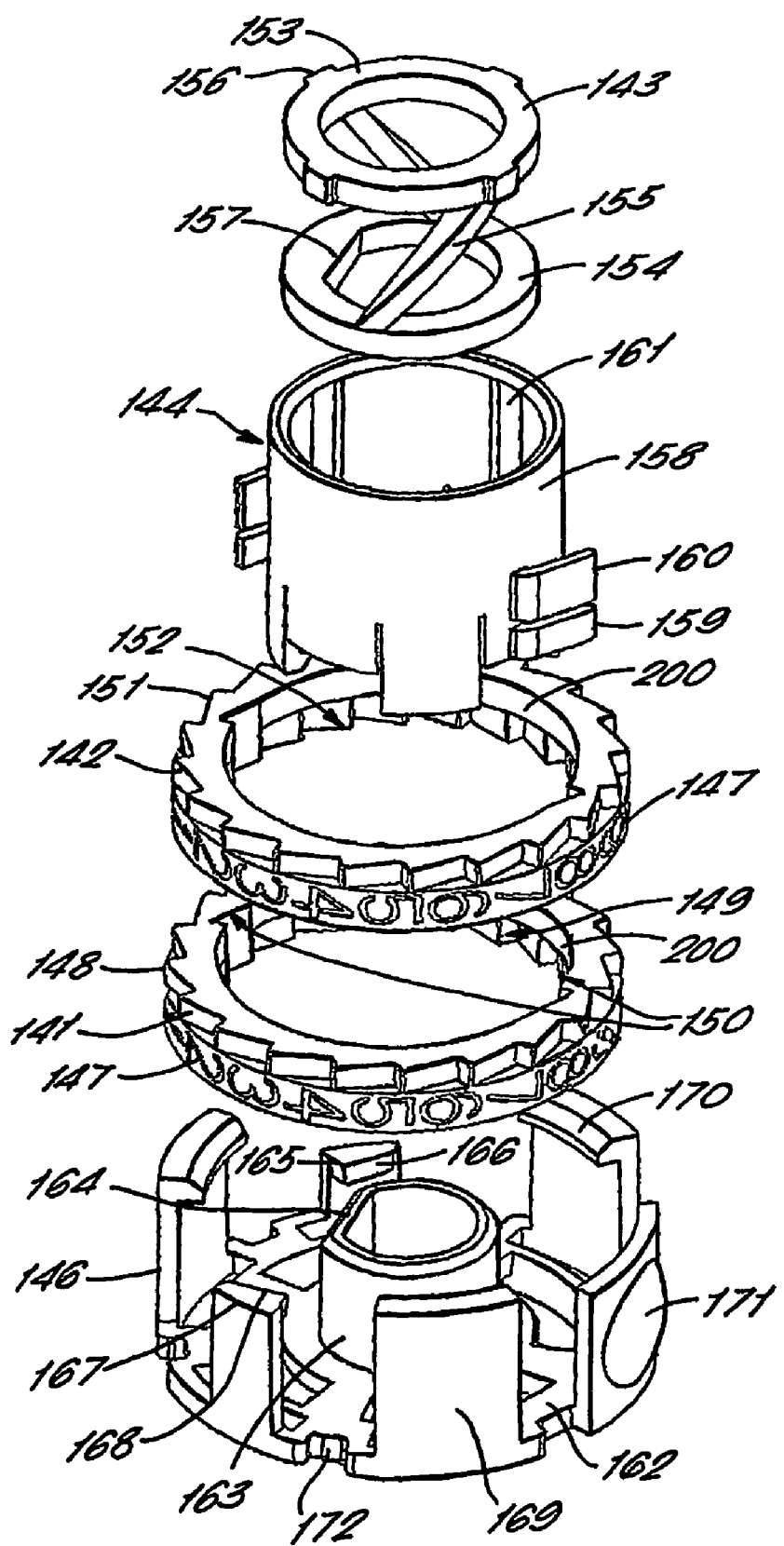

An embodiment of the present invention will now be described, by way of example only, with reference to the accompanying drawings, in which:

FIG. 1 is a cross-sectional view of a dispensing apparatus according to the present invention; and FIG. 2 is an exploded perspective view of part of the dispensing apparatus of FIG. 3.

In the following description, the invention will be illustrated, by way of example only, with respect to a pressurised dispensing container capable of delivering successive doses of a product in an aerosol form.

FIGS. 1 and 2 illustrate a dispensing apparatus according to the present invention.

The dispensing apparatus comprises a housing 1 having a cylindrical portion 2 with upper and lower ends. The upper end 6 is open whilst the lower end is closed off by a basal wall portion 7. A mouthpiece 3 which communicates with the cylindrical portion 2, depends laterally from the lower end of the cylindrical portion 2. The mouthpiece 3 defines an outlet duct 4 which terminates in an outlet 5 of the mouthpiece 3.

An inwardly directed valve stem receiving block 9 is integrally formed with the basal wall portion 7 and has its longitudinal axis aligned co-axially with a longitudinal axis of the cylindrical portion 2 of the housing 1. The valve stem receiving block 9 defines a receiving bore 12 which is open to the cylindrical portion 2 and an orifice 10 which is open to the outlet duct 4 of the mouthpiece 3. The receiving bore 12 and orifice 10 are linked by a duct 11.

Eight circumferentially spaced inwardly directed longitudinal ribs 14 are provided on the internal wall of the cylindrical portion 2.

In use a pressurised dispensing container 20 is received in the cylindrical portion 2. The pressurised dispensing container 20 comprises a canister body 21 defining a storage chamber for housing the product to be dispensed. The canister body 21 is closed off at one end by a metering valve (not shown) having a valve stem 22 which extends externally from the metering valve. The metering valve is retained in the canister body by a crimped ferrule 23.

When the pressurised dispensing container 20 is inserted into the housing 1, the valve stem 22 is received in receiving bore 12 of the valve stem receiving block 9. An annular air gap 13 exists between the internal wall of the cylindrical portion 2 and the canister body 21 to allow air to flow through the dispensing apparatus in use.

According to the present invention, a dosage counter is provided comprising first and second indicator wheels 141, 142, a helical coil 143, drum 144 and support 146. The first and second indicator wheels 141, 142 comprise indicia 147 marked on their peripheral walls. The first indicator wheel 141 denotes numerical 'units' and the second indicator wheel 142 denotes numerical 'tens'. Each indicator wheel 141, 142 is annular.

Each indicator wheel 141, 142 comprises a series of external teeth 148, 151 arranged around an upper half of the external rim of the annulus. In addition, each wheel 141, 142 comprises a series of internal teeth 149, 152 arranged around a lower half of the internal rim 200 of the annulus. The first indicator wheel 141 also comprises two diametrically opposed radial notches 150 on the upper half of the internal rim 200 of the annulus. More than two notches 150 may be provided.

The helical coil 143 comprises an upper ring 153 and a lower ring 154 which are interconnected by two flexible helical struts 155. The upper ring 153 comprises four equi-spaced radially outwardly directed protrusions. The aperture defined by the lower ring is shaped to form a key-way 157.

The drum 144 comprises a generally cylindrical body 158 having two diametrically opposed pairs of upper and lower flexible arms 160, 159 depending therefrom. An internal surface of the body 158 comprises four longitudinal recesses 161.

The support 146 comprises a generally annular base 162 from which there extends upwardly a central spigot 163 and three equi-spaced circumferentially arranged guide arms 169. The spigot 163 is shaped to form a key 164. Each of the vertical guide arms 169 comprises an inwardly directed flange 170 at its upper, distal end.

A lens unit 171 is provided dependent from the support bore 162.

A lower ratchet 165 and an upper ratchet 167 extends upwardly from the support base 162. Each ratchet 165, 167 is provided with a ramped surface 166, 168. Six notches 172 are arranged around the periphery of the support base 162.

On assembly, the first and second indicator wheels 141, 142, are received over the spigot 163 of the support base 162. The drum 144 is received within the central apertures of the two indicator wheels 141, 142. The helical coil 143 is received over spigot 163 with the key 164 of the spigot 163 engaging the key-way 157 of the lower ring 154 of the helical coil 143 so as to prevent relative rotation of the support base 162 and lower ring 154. The protrusions 156 of the upper ring 153 are slidingly received in the longitudinal recesses 161 of the drum body 158. The guide arms 169 and flanges 170 act to retain the components in axial alignment.

The support 146 is inserted in the cylindrical portion 2 of the housing 1 such that the longitudinal ribs 14 are engaged in the notches 172 of the support base 162 so as to prevent relative rotation therebetween.

The support 146 is positioned lowermost with the other components of the dosage counter being located between the support base 162 and the leading face 24 of the ferrule 23.

In use, a user operates the pressurised dispensing container 21 by depressing the canister body 21 axially to move it relative to the cylindrical portion 2 of the housing 1. As a result, the valve stem 22 is inwardly retracted relative to the metering valve such that a dose of product is dispensed from the valve stem 22 into the bore 12 and duct 11 of the valve stem receiving block 9. The product is then channelled by duct 11 and dispensed as an aerosol through orifice 10 into the outlet duct 4. The aerosol is inhaled by a user inhaling on outlet 5 of the mouthpiece 3.

The support 146 is a push-fit within the cylindrical portion 2 of the housing 1 and does not move axially during a normal operating cycle. Axial movement of the leading face 24 of the ferrule 23 is transmitted to the upper ring 153 of the helical coil 143. The upper and lower rings 153, 154 move towards each other and at the same time, due to the helical struts 155, the upper ring 153 rotates relative to the lower ring 154 which cannot rotate relative to the support base 162 due to the engagement of the key 164 and key-way 157.

As the upper ring 153 rotates, it also rotates the drum 144 due to the engagement of the protrusions 156 in the longitudinal recesses 161. As shown in FIG. 2, the drum is moved to rotate in an anti-clockwise direction.

In the assembled positions, the lower arms 159 of the drum 144 are aligned with the internal teeth 149 of the first indicator wheel 141. The upper arms 160 are partially aligned with the internal teeth 152 of the second indicator wheel 142 and partially aligned with the upper half of the internal rim 200 of the first indicator wheel 141. Hence, the lower arms 159 are always engaged with the internal teeth 149 of the first indicator wheel 141 but the upper arms 160 are normally held out of engagement with the internal teeth 152 of the second indicator wheel 142 due to the presence of the internal rim 200 of the first indicator wheel 141.

Consequently, initially when the drum 144 rotates only the first indicator wheel 141 is incrementally rotated.

After successive rotations of the first indicator wheel 141, the upper arms 160 are brought into alignment with the radial notches 150 of the first indicator wheel 141. As a consequence, the upper arms 160 can flex radially outwards so as to engage the internal teeth 152 of the second indicator wheel 142. Consequently, the second indicator wheel 142 rotates one increment on the next actuation of the metering valve. In this way, the 'tens' indicia can be incremented once for every ten increments of the 'units' indicia.

On release of the canister body 21 by the user, the pressurised dispensing container 20 returns to its rest position due to the internal spring bias of the metering valve. At the same time, the helical coil 143 recovers to its original shape rotating the drum 144 clockwise. The indicator wheels 141, 142 are prevented from rotating clockwise by the action of the lower and upper ratchets 165, 167 on the external teeth 148, 151 of the first and second indicator wheels 141, 142 respectively.

The dosage counter is 'set' in the housing 1 on the first actuation as follows:

The support 146 is assembled in the cylindrical portion 2 of the housing 1 at a point above its normal operating position, i.e., nearer the open end 6 of the housing 1 than shown in FIG. 1.

Consequently, the first and second indicator wheels 141, 142, helical coil 143 and drum 144 are all also nearer the open end 6 than their normal operating positions. On the first actuation, which may be undertaken by the user or at the point of manufacture or sale, the leading face 24 of the ferrule 23 initially axially moves the helical coil 143 without moving the support 146. Once the helical coil 143 has been completely compressed and the drum 144 incrementally rotated (during which movement the metering valve is actuated), the user, pharmacist or manufacturer applies a higher axial force to the canister body 21 to move both the helical coil 143 and support 146 axially until the retracted valve stem 22 'grounds' against the base of the receiving bore 12 of the valve stem receiving block 9. The support 146 is now in its normal operating position and is 'set'. The setting of the support 146 takes into account any variations in distance between the leading face 24 of the ferrule 23 and the end of the valve stem 22. Without this feature, it is possible for variations in pressurised dispensing containers to mean that in certain circumstances, the metering valve may be actuated before the first indicator wheel 141 rotates or vice versa.

The invention claimed is:

1. Apparatus comprising a housing defining a portion for receiving in use a dose-dispensing container, the housing containing a dose counter comprising at least one annular counter member, a helix-like coil and transmission means for operatively connecting the helix-like coil and the at least one annular counter member, wherein movement of the received dose-dispensing container acts to compress the helix-like coil to thereby rotate the transmission means and the at least one annular counter member.

2. Apparatus as claimed in claim 1 wherein the helix-like coil comprises an upper ring, a lower ring and at least one strut spanning between the upper and lower rings.

3. Apparatus as claimed in claim 2 wherein the at least one strut is helically shaped.

4. Apparatus as claimed in claim 1 wherein each of the at least one annular counter members comprise a first series of teeth, the transmission means comprising protrusions selectively engagable with each of the first series of teeth such that rotational movement of the transmission means causes the at least one annular counter member to rotate relative to the housing in a first direction.

5. Apparatus as claimed in claim 4 wherein the first series of teeth are formed around an inner rim of the at least one annular counter members.

6. Apparatus as claimed in claim 1 wherein the dose counter comprises two or more annular counter members.

7. Apparatus as claimed in claim 6 wherein the transmission means comprises a drum having the protrusions dependent therefrom, wherein one end of the helix-like coil is rotationally fixed relative to the housing and the other end of the coil is engaged with the drum, such that movement of the received dose-dispensing container compresses the helix-like coil to thereby rotate the drum.

8. Apparatus as claimed in claim 7 wherein one of the upper or lower rings of the helix-like coil comprises at least one protrusion engageable in at least one slot formed in the drum.

9. Apparatus as claimed in claim 6 wherein a first annular counter member is driven to incrementally rotate in the first direction on each actuation of the received dose-dispensing container and a second annular counter member is driven to incrementally rotate in the first direction only after a pre-determined number of incremental rotations of the first annular counter member.

10. Apparatus as claimed in claim 9 wherein a bearing surface is provided forming at least part of the inner rim of the first annular counting member to selectively hold the drum protrusions out of engagement with the first series of teeth of the second annular counter member, the bearing surface comprising at least one indent allowing movement of the drum protrusions radially outwardly into engagement with the first series of teeth of the second annular counter member after a pre-determined number of incremental rotations of the first annular counter member.

11. Apparatus as claimed in claim 1 further comprising a support slidably received in the housing to support the at least one annular counter member, helix-like coil and transmission means in proper alignment.

12. Apparatus as claimed in claim 11 wherein the support is located in a lower end of the dose dispensing container receiving portion of the housing.

13. Apparatus as claimed in claim 12 wherein the support comprises at least one ratchet engagable with a second series of teeth formed on each of the annular counter members, so as to prevent rotation of the annular counter members in a direction opposed to the first direction.

14. Apparatus as claimed in claim 11 wherein a lens is provided in the support.

15. Apparatus comprising a housing defining a portion for receiving in use a dose-dispensing container, the housing containing a dose counter comprising at least one annular counter member, a helix-like coil and transmission means for operatively connecting the helix-like coil and the at least one annular counter member, and a support for supporting the at least one annular counter member, helix-like coil and transmission means in proper alignment with the received dose-dispensing container, wherein the support is an interference fit in the housing such that a first actuation of the received dose-dispensing container sets the position of the support relative to the received dose-dispensing container and housing.

16. Apparatus as claimed in claim 1, wherein said transmission means is rotated via a rotative force of said helix-like coil.

17. Apparatus as claimed in claim 16, wherein the helix-like coil comprises an upper ring, a lower ring and at least one strut spanning between the upper and lower rings, and wherein one of said upper and lower rings is fixed from rotative adjustment and a second of said upper and lower rings imparts the rotative force on said transmission means.

18. Apparatus as claimed in claim 17 wherein said helix-like coil is received within said transmission means and the second of said upper and lower rings is axially adjustable within said transmission means.

19. Apparatus as claimed in claim 18 wherein said transmission means comprises a cylindrical drum.

20. Apparatus as claimed in claim 19 wherein said cylindrical drum and the second of said upper and lower rings share a protrusion and a slot receiving protrusion combination, with said protrusion being axially slidable in the slot upon said helix-like coil being placed in a state of compression.

* * * * *